United States Patent [19]

Hansen

[11] Patent Number: 4,826,767

[45] Date of Patent: May 2, 1989

[54] ENZYMATIC SYNTHESIS OF WAXES

[75] Inventor: Tomas T. Hansen, Allerød, Denmark

[73] Assignee: Novo Industri A/S, Bagsvaerd, Denmark

[21] Appl. No.: 925,618

[22] Filed: Oct. 31, 1986

[30] Foreign Application Priority Data

May 2, 1986 [JP] Japan ................................ 61-101198

[51] Int. Cl.⁴ ........................... C12P 7/62; C12P 7/64
[52] U.S. Cl. .................................... 435/134; 435/135; 435/176; 435/177; 435/198; 435/931
[58] Field of Search ............... 435/134, 135, 198, 931, 435/176, 177

[56] References Cited

U.S. PATENT DOCUMENTS 4,451,565  5/1984  Gratfield et al. .................. 435/117

FOREIGN PATENT DOCUMENTS 3312214  10/1984  Fed. Rep. of Germany .
12291  9/1986  Japan ................................. 435/134
58992  3/1987  Japan ................................. 435/134
2188057  9/1987  United Kingdom ................ 435/134

Primary Examiner—Sidney Marantz
Assistant Examiner—Timothy M. McMahon
Attorney, Agent, or Firm—Morris Fidelman; Franklin D. Wolffe

[57] ABSTRACT

Process for generating an about 98% ester yield from fatty acids and fatty alcohols comprising esterifying the acid and alcohol in liquid phase under a vacuum of at least 0.5 bar in the presence of an immobilized lipase.

7 Claims, No Drawings

ENZYMATIC SYNTHESIS OF WAXES

This invention relates to a enzyme catalyzed synthesis of waxes and, in particular, to synthesis in yields exceeding about 98%.

Within the context of this invention, wax may be defined as the ester of a high molecular weight acid with a high molecular weight alcohol. Contemplated are the higher fatty alcohols and acids with an alkyl chain length of at least $C_{10}$ for each.

BACKGROUND OF THE INVENTION

Waxes are a known industrial product of particular value in the cosmetic industry. In specific, liquid wax from the sperm whale has long been a valuable industrial product, especially for the cosmetic industry. As most countries now have forbidden hunting of sperm whales, alternatives for this animal source liquid wax have been sought. It has been found that a desert bush (*Simmondsi chinensis*) contains a wax ester mixture (jojoba oil), which is considered an excellent substitute for the sperm whale oil in the cosmetic, lubricant, and surfactant industries. However, several years lapse between planting of a jojoba bush and the first harvest. Thus, availability of jojoba oil is scarce and poorly adapted to market changes, and also, the yield of jojoba oil from the bush is low.

Since higher fatty acids and alcohols are commercially available from other source materials, some even being relatively inexpensive, synthesis of commercially valuable waxes is a realistic possibility.

The principal object of this invention is to provide a process for synthesizing waxes wherein the immediate reaction product constitutes a commercially acceptable wax.

RATIONALE OF THE INVENTION

Direct chemical synthesis of wax from the alcohol and fatty acid employing inorganic catalysts have long been known to the art. Unfortunately, such esterification processes normally involve excessively high temperature levels for the reaction which, aside from the energy expense, generate degradation products. Enzyme catalyzed synthesis, which can be conducted at room temperatures, offer greater hope for obtaining fatty acid esters including the desired waxes. The art has recognized that lipases can catalyze ester formation.

In particular, the Gatfield et al. U.S. Pat. No. 4,451,565 relates to an enzyme mediated synthesis of esters employing a lipase, and conducted in the absence of water. The Patentees prefer conduct of the reaction at room temperature and without presence of a solvent, but indicate that a solvent might sometimes be desirable. Knox et al. describe "Synthesis of Long-Chain Esters in a Loop Reaction System Using A Fungal Cell Bound Enzyme" in Process Biochemistry, October 1984, pp. 188 ff. Knox et al. recognized the desirability of removing water from the reaction mixture.

However, neither Gatfield et al. nor Knox et al. nor any other prior art, of which the inventor hereof is aware, produced a synthesis reaction product that itself could be a commercially acceptable wax. Need to recover the synthesized ester from substantial proportions of unreacted fatty acid and/or the alcohol constitutes a serious impediment to a commercially usable process.

The objective of this invention, which is to produce a reaction product that can be sold as a wax, can be achieved only by a process which will almost completely esterify the acid and alcohol. High purity in a wax product is, of course, desirable, but a 100% pure product is neither necessary for most uses of waxes nor are users willing to pay for extreme purity. By and large, 98% or thereabouts ester product yield is acceptable to wax users. It may be noted that the cosmetic industry will accept small levels of fatty acid and/or alcohol as impurities in the wax, and, therefore, can accept a reaction product of about 98% ester yield therein.

Some water apparently is required for the proper action of the lipase enzyme, and water is a reaction product of the esterification, yet presence of water influences the reaction equilibrium. Insofar as the inventor is aware, it was not known for certain heretofore that 98% yield from an enzymatic esterification could be obtained.

BRIEF STATEMENT OF THE INVENTION

Briefly stated, the process of the present invention comprises esterifying essentially non-volatile monohydric alcohols and mono-basic acids, preferably a higher fatty alcohol and a higher fatty acid in liquid phase in the presence of an immobilized lipase under evacuated conditions wherein the pressure is less than about 0.5 bar, preferably less than about 0.2 bar.

Under these conditions the reaction proceeds to very near completion i.e., to about 98%; sometimes more.

A preferred temperature range is 60°–80° C. Preferred reactants are oleic acid and oleyl alcohol.

Surprisingly, the initial water content in the enzyme preparation is not crucial since the evacuated conditions remove any excess water in the enzyme as well as the water produced by the esterification. Also, the quantity of enzyme employed in the reaction mixture has not been found to be critical, inasmuch as reducing the proportion of the enzyme in the mixture can be compensated for by increase in reaction time.

Surprisingly, the temperature level at which the reaction was conducted did not affect the final yield point, nor within 60°–80° C. did temperature seem to have a particularly material effect on the reaction rate.

A suitable particle size for practice of this invention is in the range of about 0.1-2 mm for the immobilized lipases. Removal of the immobilized enzyme from the reaction product by filtration is contemplated The preferred enzyme is the *Mucor miehei* lipase immobilized on particle form ion exchange resin. However, the invention is not limited to the *Mucor miehei* lipase. Satisfactory results have been obtained with the lipase from *Humicola lanuginosa* and *Candida antarctica*, the latter being a recently discovered lipase described in Denmark Application Nos. 4965/86 and 4966/86 filed Oct. 16, 1986.

DISCUSSION OF THE INVENTION

Water content is a principal uncertainty with regard to obtaining about 98% ester yield in the reaction product, as may be seen from the following generalized formula for wax synthesis:

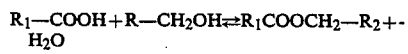

wherein $R_1$ and $R_2$ are each at least a nine carbon alkyl chain.

As is well known in the art, the reaction equilibrium can be forced to the right namely, toward higher proportions of ester product in the reaction mixture through removal of the water already present or formed by the esterification reaction. Such can be accomplished by vacuum conditions and/or heat. However, water is necessary to retain the enzymatic activity of the lipase.

It may be noted that ordinarily a lipase hydrolyzes the ester linkage. However, lipase is known to catalyze the formation of esters, provided water content in the reaction mixture is low. See, for example, the aforementioned U.S. Pat. No. 4,451,565 and the Knox et al. Paper.

Conduct of the esterification in the presence of a lipase without concomitant water removal, limits the yield. Something less than about 90% ester yield seems to be the maximum yield obtainable without water removal. However, when vacuum is applied and an immobilized lipase is employed, the system seems to change quite sharply. The immobilized enzyme apparently retains water in sufficient content to activate the enzyme regardless of the level of vacuum applied. Moreover, the water retained by the immobilized enzyme does not appear to take part in establishing the reaction equilibrium. Desirably, even the initial water content of the immobilized enzyme does not seem to affect the reaction equilibrium. For example, it has been found that an initial water content variation of 2% to 20% by weight in the immobilized lipase preparation has essentially no effect on the final yield equilibrium of the esterification reaction.

It is believed, therefore, that during the course of the esterification reaction, any and all water evolved by the reaction or from the enzyme becomes removed from the reaction mass by the vacuum. If a high water content lipase preparation is employed, water content of the enzyme decreases. Alternatively, if a very dry lipase preparation is employed, some of the reaction water becomes incorporated in the lipase preparation. Depending on the operating temperature and the degree of vacuum applied, the final water content in the lipase preparation will vary within a 4–7% by weight range. In any event, once the water content in the lipase preparation falls to some level between about 4–7%, it remains in that range. Either an equilibrium water content in the immobilized enzyme becomes established, or possibly, the reason for the 4–7% water content is that the rate at which the vacuum removes this residual water from the enzyme is so slow as to not be material over the time span during which the esterification reaction takes place.

Effectively, a very desirable situation occurs, namely, sufficient water to activate the lipase, yet the yield results evidence that the water produced by the esterification along with any excess water initially introduced into the reaction mixture is removed by the vacuum.

Conduct of esterification under vacuum conditions, so as to remove the water of reaction, is most easily accomplished for a batch reaction. However, practice of this invention is not limited to batch reactions. Continuous feed stirred tank reaction systems (CFSTR) can be operated under evacuated conditions. Even fluidized bed or packed bed column reactor systems can be constructed to operate under the moderate level of vacuum employed for the present process.

One consequence of conducting esterifcation under the vacuum conditions of 0.2 bar or less is that presence of volatile solvents in the reaction mixture becomes relatively undesirable. The solvents would evaporate, then need to be replaced, or recovered and recycled. Inclusion of an azeotrope former, such as hexane has not been found necessary to remove the water of reaction. Vacuum alone suffices. Employment of a volatile reactant, e.g., methanol, ethanol, isoproponal offers the same complications to the reaction system as presence of a volatile solvent. Fortunately the $C_{10}$ fatty alcohols and fatty acids are essentially non-volatile at the vacuum and temperature conditions are contemplated for practice of this invention.

Esterifying at temperature levels above ambient temperature facilitates removal of water of reaction, and such is contemplated in practice of this invention. Preferred is reaction temperatures above about 50° C., and 60° C.–80° C. constitutes the preferred range. The melting point of each reactant, which often is above ambient temperature, constitutes the lower temperature limit for operability of the process.

The consequence of esterifying at higher than ambient temperature is, of course, increased volatility of the water content and, also a more rapid reaction rate, both of which are desirable. No shift in the ultimate reaction equilibrium has been found. The equilibrium ester synthesis yield appears to be the same throughout the preferred 60°–80° C. range. Even at temperatures below the 60°–80° range preferred for the practice of this invention, the final equilibrium appears to be the same. This consequence confirms the inventor's belief that even moderate levels of vacuum are effective to remove all water that might affect the reaction equilibrium.

Accordingly, the particular reaction temperature selected for conduct of any specific ester synthesis may be based on considerations other than the ester yield of about 98% contemplated for practice of this invention. Considerations for selection of reaction temperature are: activity and stability of the lipase preparation (for which an optimum temperature level often exists); the desirability of having a fluid reaction mixture, and in particular, of having a reaction mixture for which viscosity is reasonably low so that mixing of the reactants and water vapor release is facilitated. Also, since reaction velocity does decrease with temperature, the time required for the reaction mixture to attain the 98% ester yield level is affected by temperature, which is to say that selection of the operating temperature might well be based on what is a reasonable reaction time.

Conduct of the esterification reaction in the 60°–80° C. temperature range, as is preferred for practice of this invention, does have some particular advantages. Specifically, this is a range in which the raw materials, namely, the $C_{10+}$ fatty acids and $C_{10+}$ monohydric alcohols and the product wax are liquid phase relatively fluid materials. It becomes possible then to terminate the reaction and promptly filter the still warm reaction mass to remove the lipase preparation. This generates a reaction product that itself constitutes a 98% ester yield product that may be sold to users of the wax.

As may be inferred from the foregoing discussion, a preferred mode of this invention is an equimolar reaction which, in turn, eliminates the need either to remove the reactant in excess or to provide a product containing one reactant as a major impurity. However, within contemplation of practice of the invention is a modest deviation from equimolar reactants. One of the reactants, but not the other, may be wanted as an impurity in the wax, for example, a slight excess of the alcohol may be employed when only such is desired in the ultimate product. Thus, in practice of this invention, the acid to alcohol ratio may range from 1.1:1 to 0.9:1, with equimolar preferred.

Inasmuch as the objective of this invention is to obtain a reaction mixture that itself may be a commercially acceptable product, it may be noted that neither the fatty acid nor the alcohol need be pure in more than a technical sense, say 70% purity. In total, the reaction product of the process is of purity that approximates the purity of the initial reactants.

A preferred lipase for practice of this invention is the *Mucor miehei* lipase and preferred immobilized forms are those described in DENMARK Patent Application Nos. 4167/84 and 878/85. These lipase forms are particularly advantageous since the immobilized lipase preparations constitute particles that are in the size range of 0.1-1 mm, a size range adapted to filtration removal of the lipase from the reaction mixture.

It is, of course, desirable to remove the enzyme from the reaction mixture since otherwise the enzyme would form an insoluble solid impurity therein. As a practical matter, recovery of the enzyme is desirable since multiple re-uses of the enzyme are possible. In the experimentation from which this invention ensued, the immobilized lipase was re-employed at least five times. Accordingly, the preferred immobilized lipase preparation has the advantage of facile removal from the reaction produces and of multiple re-use.

Mention has already been made that this invention is directed to enzymatic synthesis of waxes, namely esters of $C_{10}$ or more fatty acids with alkyl $C_{10}$ or more monohydric alcohols. Either the acid or the alcohol may be fully saturated or contain 1-6 double bonds. The enzymatic action of lipase is specific, and the reactants as well as the resulting waxes are stable at the highest reaction temperature of 80° C. contemplated for practice of this invention. It may be noted that fully saturated fatty acids and waxes have melting points not far below 80° C. The ester of oleyl alcohol and oleic acid is a preferred product of the process. Both reactants are commercially available and the oleyl oleate product may be substituted for jojoba oil.

The following Examples illustrate the invention. In all of the Examples, esterification was carried out using a rotating vacuum evaporator. The degree of ester formation was followed by measuring the acid value (IUPAC standard methods oil and fats, 2.201), i.e., titrate the remaining free fatty acids. The degree of synthesis was calculated as:

$$\% \text{ ester} = \frac{AV_0 - AV}{AV_0} \quad \begin{array}{l} AV \text{ is acid value of the mixture} \\ AV_0 \text{ is initial acid value} \end{array}$$

LIPOZYME ™ enzyme (about 20,000 LU per gram) employed in conduct of the Examples is *Mucor miehei* lipase adsorbed on Duolite ES 562, made as described in DENMARK Patent Application No. 4167/84.

EXAMPLE 1

Synthesis of Long Chain Aliphatic Esters With and Without Simultaneous Removal of the Co-produced Water A fatty acid and a fatty alcohol (0.05 mol each) are put into a flask together with 2 g of LIPOZYME ™. The flask is rotated at 70° C. and 45 mm Hg for three hours. The results appear in Table I.

The run was repeated without application of vacuum. The results appear in Table II.

TABLE I

| Acid | Alcohol | % Ester Synt. | | |
|---|---|---|---|---|
| | | 1 h | 2 h | 3 h |
| Oleic Acid | Oleyl Alcohol | 80.1 | 98.3 | 99.7 |
| Lauric Acid | Stearyl Alcohol | 67.4 | 95.0 | 96.1 |

TABLE II

| Acid | Alcohol | % Ester Synt. | | |
|---|---|---|---|---|
| | | 1 h | 2 h | 3 h |
| Oleic Acid | Oleyl Alcohol | 75 | 82 | 84 |
| Lauric Acid | Stearyl Alcohol | 73 | 81 | 84 |

The presence of water in the reaction mixture favors the hydrolysis of the esters, i.e., the equilibrium is reached at a lower conversion into the ester. The observed activity of LIPOZYME ™ decreases when it is hydrated by the co-produced water. This appears from a comparison of Table I and Table II.

EXAMPLE 2

Synthesis at Various Vacuum Levels

The substrate was: 11.4 g (0.05 mol of myristic acid (MERCK, purity >98%) and 10.7 g (0.05 mol) of myristylalcohol (MERCK, purity >98%). Temperature was 70° C. Enzyme dosage was 1.0 g of LIPOZYME ™ on dry substance basis. (Initial water content was 8%.) Several different pressures were tested and the degree of synthesis measured as % yield.

| Reaction Time | Total Pressure | | | | |
|---|---|---|---|---|---|
| | 1.0 bar | 0.5 bar | 0.2 bar | 0.05 bar | 0.005 bar |
| ½ hour | 53.1 | 51.0 | 62.6 | 51.3 | 48.1 |
| 1 hour | 72.6 | 83.4 | 86.0 | 85.8 | 87.8 |
| 2 hours | 85.5 | 97.4 | 95.2 | 98.8 | 98.0 |
| 3 hours | 88.9 | 97.3 | 98.2 | 99.1 | 98.9 |
| Final Water Content in Lipase | 7.0% | 6.9% | — | 7.0% | 7.5% |

No difference on the final ester formation can be observed between 0.05 bar and 0.005 bar. Yield of 98+% was obtained at 0.2 bar.

EXAMPLE 3

Water Content of the Enzyme

Under the same conditions as in Example 2, except that 2.0 g of LIPOZYME ™ was used instead of 1.0 g and at a pressure of 0.05 bar, the influence of initial water content in the enzyme was examined.

| Reaction time | INITIAL WATER CONTENT | | | | |
|---|---|---|---|---|---|
| | 2.7% | 8.2% | 12.1% | 14.5% | 18.7% |
| ½ hour | 89.2 | 89.8 | 88.5 | 85.0 | 91.2 |
| 1 | — | 97.7 | 98.4 | 98.1 | 98.7 |
| 2 | 96.9 | 99.1 | 98.8 | 98.8 | 99.5 |
| 3 | 98.9 | 99.7 | 98.8 | 99.4 | 99.3 |
| Final water-content in lip. | 4.7% | 4.8% | 5.4% | 6.1% | 5.9% |

No relationship seems to exist between initial water content and activity.

EXAMPLE 4

Temperature Variation

Under the same conditions as in Example 2 and at a pressure at 0.05 bar the influence of temperature was examined.

| Reaction time | 60 C | 70 C | 80 C |
|---|---|---|---|
| ½ hour | 48.8 | 42.3 | 47.4 |
| 1 | 82.1 | 77.5 | 80.0 |
| 2 | 98.3 | 98.5 | 97.8 |
| 3 | 99.4 | 98.3 | 99.4 |
| Final watercont. in lipase | 4.6% | 5.2% | 3.8% |

No difference in enzyme activity was observed from 60° to 80° C.

EXAMPLE 5

Enzyme Dosage

Under the same conditions as in Example 2 and at a pressure of 0.05 bar, the influence of enzyme dosage was examined.

| | ENZYME DOSAGE | | | | |
|---|---|---|---|---|---|
| Reaction time | 0 | 0.1 g | 0.5 g | 1.0 g | 2.0 g |
| ½ hour | — | 1.5 | 24.1 | 42.3 | 89.8 |
| 1 hour | 0.0 | 5.0 | 48.2 | 77.5 | 97.7 |
| 2 | 3.0 | 9.5 | 87.6 | 98.5 | 99.1 |
| 3 | — | 22.1 | 93.3 | 98.3 | 99.7 |
| Final water-contn. in lip. | — | — | 5.7% | 5.2% | 4.8% |

(1) 2.0 g of enzyme carrier without enzyme

It can be seen that 1.0 g of immobilised lipase (4.5% w/w) should be enough to reach equillibrium within 3 hours.

EXAMPLE 6

Enzyme Re-Use

Under the same conditions as in Example 2 and at a pressure of 0.05 bar, the same immobilized enzyme was reused five times. After three hours of reaction, the product was decanted off and a fresh portion of substrate was added to the same enzyme.

| Reaction time | 1 | 2 | 3 | 4 | 5 |
|---|---|---|---|---|---|
| ½ hour | 43.4 | 56.4 | 36.8 | 51.1 | 45.3 |
| 1 | 73.6 | 78.9 | 83.3 | 81.1 | — |
| 2 | 97.2 | 97.4 | 95.7 | 97.5 | 93.3 |
| 3 | 98.3 | 98.6 | 98.4 | 97.4 | 98.6 |

It can be seen that it is possible to re-use the lipase for at least five times without observing any change in the final degree of ester synthesis.

EXAMPLE 7

Different Esters

Under the same conditions as in Example 2 and at a pressure of 0.05 bar, esterification was examined with different substrates. In all cases 0.05 moles of both fatty acid and alcohol were used.

| Reaction time | capric acid + myristyl alc. | lauric acid + myristyl alc. | palmetic acid + myristyl alc. | stearic acid + myristyl alc. | oleic acid + myristyl alc. | myristic acid + stearoyl alcohol |
|---|---|---|---|---|---|---|
| ½ hour | 20.5 | 39.6 | 34.5 | 36.8 | 45.3 | 43.1 |
| 1 | 41.5 | 78.2 | 50.8 | 69.8 | 75.2 | 79.0 |
| 2 | 90.8 | 98.4 | 97.0 | 96.0 | 94.6 | 96.8 |
| 3 | 98.5 | 98.3 | 97.8 | 97.2 | 95.8 | 97.6 |

Degree of synthesis.

It can be seen that the lipase can be used for esterifying a wide spectrum of fatty acids and fatty alcohols to an ester synthesis yield of about 98%.

EXAMPLE 8

Humicola lanuginosa Lipase

An immobilized form of the lipase from *Humicola lanuginosa* was made in the same way as the immobilized lipase from *Mucor miehei* and tested as described in Example 2 at the pressure of 0.05 bar.

| Reaction Time | % Synthesis |
|---|---|
| 1 hour | 16.2 |
| 2 hours | 22.4 |
| 3 hours | 46.9 |
| 4 hours | 73.8 |
| 5 hours | 91.9 |
| 6 hours | 94.9 |
| 7 hours | 96.3 |

It can be seen also that the lipase from *Humicola lanuginosa* can be used for wax ester synthesis. The rate at which yield continued to improve after the fifth hour indicates that the desired about 98% yield is attainable, e.g., through longer reaction times.

EXAMPLE 9

Candida antarctica lipase

An immobilized form of the lipase from *Candida antarctica* was made in the same way as the immobilized lipase from *Mucor miehei* with, however, loading of 9300 LU/g and tested as described in Example 2 at the pressure of 0.05 bar using, however, an enzyme dosage of 2g of the immobilized lipase and a test temperature of 60° C.

| Reaction Time | % Synthesis |
|---|---|
| ½ hour | 78.6 |
| 1 hour | 96.7 |
| 2 hours | 98.7 |

I claim:

1. A process for generating a wax which comprises: reacting a liquid mixture of high molecular weight acid and high molecular weight alcohol in molar proportion of from 0.9:1 to 1:0.9 in the presence of a particulate immobilized lipase at a pressure not exceeding about 0.5 bar, whereby water vapor is removed from the reaction mixture by the sub-atmospheric pressure, carrying out the reaction until at least about a 98% ester yield results, the acid, alcohol and ester all being essentially nonvolatile at the prevailing sub-atmospheric pressure, and thereafter removing the particulate immobilized lipase from the reaction product.

2. A process according to claim 1 wherein the reaction temperature is in the range of 60° C.–80° C. and the pressure does not exceed about 0.2 bar.

3. A process according to claim 1 wherein the reaction mixture is equimolar.

4. A process according to claim 1 further comprising reacting a fatty alcohol and a fatty acid.

5. A process according to claim 4 wherein said alcohol and said acid are oleyl alcohol and oleic acid.

6. A process according to claim 1 wherein the particle size of said particulate immobilized lipase preparation is 0.1–1 mm in diameter.

7. A process according to claim 1 wherein the lipase of *Mucor miehei* is employed.

* * * * *

UNITED STATES PATENT AND TRADEMARK OFFICE
CERTIFICATE OF CORRECTION

PATENT NO. : 4,826,767

DATED : May 2, 1989

INVENTOR(S) : Tomas T. Hansen

It is certified that error appears in the above-identified patent and that said Letters Patent is hereby corrected as shown below:

Col. 5, line 28, "duces" should read "ducts".

Example 5, col. 7, "Reaction time 0    0.1g" should read "Reaction time $0^{(1)}$    0.1g".

Signed and Sealed this

Fourteenth Day of August, 1990

*Attest:*

HARRY F. MANBECK, JR.

*Attesting Officer*     *Commissioner of Patents and Trademarks*